United States Patent
Grant

(10) Patent No.: US 8,598,235 B2
(45) Date of Patent: Dec. 3, 2013

(54) TREATING IMPULSE CONTROL DISORDERS WITH CATECHOL-O-METHYL-TRANSFERASE INHIBITORS

(76) Inventor: Jon E. Grant, St. Paul, MN (US)

( * ) Notice: Subject to any disclaimer, the term of this patent is extended or adjusted under 35 U.S.C. 154(b) by 223 days.

(21) Appl. No.: 12/960,049

(22) Filed: Dec. 3, 2010

(65) Prior Publication Data

US 2012/0004316 A1  Jan. 5, 2012

Related U.S. Application Data

(60) Provisional application No. 61/266,834, filed on Dec. 4, 2009.

(51) Int. Cl.
*A61K 31/135* (2006.01)
*A61K 31/12* (2006.01)

(52) U.S. Cl.
USPC .......................................... 514/654; 514/676

(58) Field of Classification Search
None
See application file for complete search history.

(56) References Cited

U.S. PATENT DOCUMENTS

| | | | |
|---|---|---|---|
| 4,938,949 | A | 7/1990 | Borch et al. |
| 5,780,479 | A | 7/1998 | Kim |
| 7,825,135 | B2 | 11/2010 | Blackaby et al. |
| 2001/0023254 | A1 | 9/2001 | McElroy |
| 2004/0077650 | A1 | 4/2004 | Dow |
| 2009/0012177 | A1 | 1/2009 | Shafa et al. |
| 2009/0054437 | A1 | 2/2009 | Learmonth et al. |
| 2010/0113529 | A1 | 5/2010 | Learmonth et al. |
| 2010/0120752 | A1 | 5/2010 | DeBruin et al. |
| 2010/0168113 | A1 | 7/2010 | Learmonth et al. |

FOREIGN PATENT DOCUMENTS

| | | |
|---|---|---|
| EP | 1541197 | 6/2005 |
| EP | 1845097 | 10/2007 |
| JP | 2005-126402 | 5/2005 |
| JP | 2005126402 | 5/2005 |
| WO | 92/18005 | 10/1992 |
| WO | 94/13659 | 6/1994 |
| WO | 02/43731 | 6/2002 |
| WO | 2007/013830 | 2/2007 |
| WO | 2008/051610 | 5/2008 |
| WO | 2008/094053 | 8/2008 |
| WO | 2010/014025 | 2/2010 |

OTHER PUBLICATIONS

Factor (J Am Soc Exp NeuroTherap 5:164-180, 2008).*
English-language Machine Translation of JP 2005-126402, Industrial Property Digital Library, Japan Patent Office, 27 pages.
PCT International Search Report for International Application No. PCT/US2010/058907, mailed May 24, 2011, 4 pages.

* cited by examiner

*Primary Examiner* — Craig Ricci
(74) *Attorney, Agent, or Firm* — Kagan Binder, PLLC

(57) ABSTRACT

The invention provides methods for treating impulse control disorders in patients with catechol-o-methyl-transferase inhibitors. The invention also provides methods for treating patients with obsessive compulsive disorders and substance addictions with catechol-o-methyl-transferase inhibitors.

4 Claims, No Drawings

TREATING IMPULSE CONTROL DISORDERS WITH CATECHOL-O-METHYL-TRANSFERASE INHIBITORS

CROSS-REFERENCES TO RELATED APPLICATIONS

This application claims the benefit of U.S. Provisional Patent Application No. 61/266,834, filed on Dec. 4, 2009, entitled "CATECHOL-O-METHYL-TRANSFERASE INHIBITORS FOR TREATING IMPULSE CONTROL DISORDERS," which is incorporated herein by reference in its entirety.

BACKGROUND

The present disclosure is generally directed to the novel use of catechol-o-methyl-transferase inhibitors (COMT inhibitors) for the treatment, amelioration or prevention of impulse control disorders. An impulsive person is apt to exhibit impulsive behavior often associated with a lack of self-control.

Impulse control disorders (ICD) are characterized by the failure to resist an impulse, drive or temptation to perform an act that is harmful to the person or to others. In most cases, the individual feels an increasing sense of tension or arousal before committing the act, and then experiences pleasure, gratification, or release at the time of committing the act. After the act is performed, there may or may not be regret or guilt. ICD, therefore, have a substantial impact on individuals as well as on society.

ICD are a separate group of psychiatric disorders, listed in the "Diagnostic and Statistical Manual of Mental Disorders" (DSM-IV) of the American Psychiatric Association as a residual category consisting of impulse control disorders 'Not Elsewhere Classified' (NEC) and impulse control disorders 'Not Otherwise Specified' (NOS). The first includes: intermittent explosive disorder, pyromania, kleptomania, pathological gambling and trichotillomania. No specific disorders are mentioned in DSM-IV under the heading: "impulse control disorders NOS", but this group is defined as "a category for disorders of impulse control that do not meet the criteria for any specific impulse control disorder or for any other mental disorder having features involving impulse control (such as borderline, antisocial, histrionic and narcissistic personality disorders)". In the scientific and patent literature a number of such impulse control disorders, also referred to as "atypical impulse control disorders", are described, for instance: compulsive buying disorder, binge eating and binge drinking disorders, impulsive self-injurious behavior, such as pathological skin picking, nail-biting and nose-picking, gouging, head banging and self-biting, paraphilic sexual addictions, and lack of control of a person's sexual impulses.

Patients suffering from an impulse control disorder have to date been treated by psychotherapy, behavior modification, hypnosis, relaxation therapy and administration of varied pharmaceutical preparations, the latter with little or no success. Historically, impulse control disorders have been considered refractory to known pharmacological or psychotherapeutic treatments. Therefore, a continuing need exists for agents that will be effective to treat the symptoms associated with ICD, either by eliminating or by reducing them.

In different patent and patent applications a variety of molecular mechanisms are reported to be of therapeutic value in impulse control disorders: opioid antagonists (U.S. Pat. No. 5,780,479), anticonvulsants (WO 02/43731); serotonin antagonists (US 2001/023254); 5-HT1A agonists (WO 94/13659), serotonin reuptake inhibitors (WO 92/18005), cannabinoid antagonists (US 2004/0077650), muscarinic agonists (US 2010/0120752), selected adrenergic agonists and adrenergic receptor antagonists (WO 08/51610) and heteroaryl piperdine glycine transport inhibitors (U.S. Pat. No. 7,825,135). COMT inhibitors, specifically tolcapone and entacapone, have been reported to treat certain psychiatric disorders such as schizophrenia, major depression, bipolar disorder, substance dependency and to combat cravings associated with substance abuse (US 2009/0012177). These disorders are distinct from impulse control disorders (DSM-IV).

SUMMARY OF THE INVENTION

Certain embodiments of the present invention provide methods for treating an impulse control disorder in a patient in need of such treatment, comprising administering to the patient a therapeutically effective amount of a catechol-O-methyl-transferase inhibitor (COMT inhibitor).

Certain embodiments of the present invention provide methods for treating obsessive compulsive disorder in a patient in need of such treatment, comprising administering to the patient a therapeutically effective amount of a catechol-O-methyl-transferase (COMT) inhibitor.

Certain embodiments of the present invention provide methods for treating a substance addiction in a patient in need of such treatment, comprising administering to the patient a therapeutically effective amount of a catechol-O-methyl-transferase (COMT) inhibitor.

In certain embodiments, the impulse control disorder is pathological gambling, binge eating, kleptomania, compulsive buying, compulsive sexual behavior, hair pulling, pyromania, skin picking, or self-injury.

In certain embodiments, the impulse control disorder is pathological gambling or kleptomania.

In certain embodiments, the COMT inhibitor is tolcapone or entacapone.

In certain embodiments, the COMT inhibitor is tolcapone.

In certain embodiments, the COMT inhibitor is entacapone.

In certain embodiments, the COMT inhibitor is administered orally.

In certain embodiments, the COMT inhibitor is administered at a dose of about 100 mg-300 mg per day.

In certain embodiments, the COMT inhibitor is administered at a dose of about 140 mg per day.

In certain embodiments, the patient is a human.
In certain embodiments, the patient is a male.
In certain embodiments, the patient is a female.

Certain embodiments of the present invention provide the use of a COMT inhibitor to prepare a medicament useful for treating an impulse control disorder in a human.

Certain embodiments of the present invention provide the use of a COMT inhibitor to prepare a medicament useful for treating obsessive compulsive disorder in an human.

Certain embodiments of the present invention provide the use of a COMT inhibitor to prepare a medicament useful for treating a substance addiction in a human.

In certain embodiments, a patient in need of treatment is a patient that has been diagnosed as suffering from, e.g., an impulse control disorder, such as pathological gambling kleptomania or binge eating disorder.

DETAILED DESCRIPTION

The present invention provide methods for the treatment of impulse control disorders (e.g., pathological gambling, binge eating, kleptomania, compulsive buying, compulsive sexual behavior, hair pulling, pyromania, skin picking, or self-injury), obsessive compulsive disorder and substance addictions such as nicotine dependence using COMT inhibitors.

Certain embodiments of the present invention provide a COMT inhibitor for use in the prophylactic or therapeutic treatment of impulse control disorders such as pathological gambling.

Other embodiments of the present invention provide methods for the treatment of obsessive compulsive disorder and substance addictions such as nicotine dependence using COMT inhibitors.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Disorders

The repeated engagement in pathologic behavior, as seen in impulse control disorders, can be conceptualized cognitively by attentional bias to impulse-related stimuli with resulting cravings, with a pattern of decision making that repeatedly ignores long-term negative consequences in order to obtain immediate gratification. Executive dysfunction in the form of diminished cognitive flexibility may underlie the problems in decision making in impulse control disorders.

Impulse control disorders include, but are not limited to, pathological gambling, binge eating, kleptomania, compulsive buying, compulsive sexual behavior, hair pulling, pyromania, skin picking, and self-injury.

Other disorders that can be treated with a COMT inhibitor are obsessive compulsive disorder and substance addictions, including nicotine dependence.

In some embodiments of the invention, pathological gambling (PG) is treated with a COMT inhibitor. PG usually begins in early adolescence in men, and between ages 20 and 40 in women. PG often involves repetitive behaviors. People with this problem have a hard time resisting or controlling the impulse to gamble. People with PG often feel ashamed and try to avoid letting others know of their problem. A patient can be diagnosed as suffering from PG by having five or more of the following symptoms:

committing crimes to get money to gamble;
feeling restless or irritable when trying to cut back or quit gambling;
gambling to escape problems or feelings of sadness or anxiety;
gambling larger amounts of money to try to make back previous losses;
having had many unsuccessful attempts to cut back or quit gambling;
losing a job, relationship, or educational or career opportunity due to gambling;
lying about the amount of time or money spent gambling;
needing to borrow money to get by due to gambling losses;
needing to gamble larger amounts of money in order to feel excitement; and
spending a lot of time thinking about gambling, such as past experiences or ways to get more money with which to gamble.

In other embodiments of the invention, kleptomania is treated with a COMT inhibitor. Kleptomania is characterized by a recurrent failure to resist impulses to steal items even though they are not needed for personal use or for their monetary value. The individual experiences a rising subjective sense of tension before the theft and feels pleasure, gratification or relief when committing the theft. The stealing is not committed to express anger or vengeance, is not done in response to a delusion or hallucination, and is not better counted for by conduct disorder, a manic episode or antisocial personality disorder. The objects are stolen despite the fact that are typically of little value to the individual who could have afforded to pay for them, and often gives them away or discards them. Although patients will generally avoid stealing when immediate arrest is probable, they usually do not preplan the thefts or fully take into account the chances of apprehension. The stealing is done without assistance from, or collaboration with, others.

In still other embodiments of the invention, binge eating disorder is treated with a COMT inhibitor. Binge eating disorder is characterized by discrete periods of binge eating during which large amounts of food are consumed in a discrete period of time. A sense of control over eating is absent. Binge eating disorder is distinguished from Bulimia Nervosa by the absence of the regular use of inappropriate compensatory behaviors such as self-induced vomiting, misuse of laxatives and other medications, fasting and excessive exercise that are characteristic of the latter. Binge drinking disorder is—mutatis mutandis—the same as binge eating disorder.

The DSM-IV provides additional information regarding impulse control disorders such as PG, kleptomania and binge eating disorder.

The effectiveness of COMT inhibitors to treat PG can be determined using known assessments, e.g., the Clinical Global Impression Scale (CGI), Yale Brown Obsessive Compulsive Scale Modified for Pathological Gambling (PG-YB-OCS), the Gambling Symptom Assessment Scale (G-SAS), the Sheehan Disability Scale (SDS), the Hamilton Anxiety Rating Scale (HAM-A), the Hamilton Depression Rating Scale (HAM-D), the Perceived Stress Scale (PSS; used at baseline and study endpoint), and the Quality of Life Inventory (QOLI; used at baseline and study endpoint).

Catechol-O-Methyl-Transferase (COMT) Inhibitors

The methylation enzyme catechol-O-methyltransferase (COMT) regulates dopamine levels in the prefrontal cortex. In the frontal cortex one of the functions of dopamine is to increase the signal to noise ratio, increased dopamine correlating with increased frontal performance. Studies of naturally occurring COMT isozymes with differential enzymatic activity have shown that the higher cortical dopamine levels associated with reduced COMT activity results in improved frontal cortical cognitive performance. Optimal dopamine modulation of prefrontal cortex networks appears to be necessary for a variety of cognitive functions, such as attention, response flexibility or working memory. In addition, prepulse inhibition reflects sensorimotor gating, a form of CNS inhibition wherein irrelevant sensory information is filtered out of processing and attention can focus more on salient features of the environment. Higher prepulse inhibition levels predict superior executive functioning. Suboptimal prefrontal cortex dopamine levels are associated with lower prepulse inhibition. Lower dopamine levels in the prefrontal cortex are also thought to contribute to deficits in cognitive processing.

Recent research has demonstrated that the val allele of COMT is associated with a 3- to 4-fold increase in enzyme activity and decreased prefrontal dopamine levels. The COMT val allele has been shown to be associated with increased susceptibility to nicotine dependence and greater risk for smoking relapse. Relapse may be related to less efficient prefrontal neural signaling and possible deficits in executive cognitive functioning. Smokers homozygous for the val allele are more sensitive to the effects of an abstinence challenge and demonstrate decrease activation in the dorsal lateral prefrontal cortex and the dorsal cingulate/medial prefrontal cortex during abstinence.

COMT inhibitors (for example, tolcapone) should increase prefrontal cortex dopamine and improve executive functioning, working memory, and cognitive flexibility. These should therefore improve decision making in individuals with impulse control disorders/addictions and enhance prefrontal efficiency.

Tolcapone enhances prefrontal cortex dopamine associated with a natural awards such as the anticipation and consumption of impulse control disorders and may confer cognitive enhancement without the unwanted side effects of increasing basal dopamine levels in cortical and subcortical regions. Tolcapone increase dopamine level in the prefrontal cortex by using the dopamine released by expectancy and consumption of the natural reward.

As described herein, administration of COMT inhibitors (e.g., tolcapone or entacapone) should improve executive functioning, working memory, and cognitive flexibility. For example, a COMT inhibitor may function within the context of the present invention by enhancing intentional inhibition of behavior. It is thought that these effects are mediated, at least in part, by an increase prefrontal cortex dopamine. COMT inhibitors should therefore improve decision making in individuals with impulse control disorders and enhance prefrontal efficiency.

A COMT inhibitor is a compound that inhibits the activity of the enzyme catechol-O-methyl transferase. Examples of COMT inhibitors are tolcapone and entacapone. Whether a compound inhibits the activity of the enzyme catechol-O-methyl transferase can be determined by the art worker using standard assays.

An example of a COMT inhibitor is tolcapone

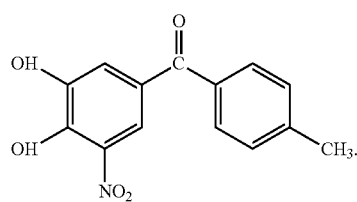 [SMILES: Cc1ccc(C(=O)c2cc(O)c(O)c([N+](=O)[O-])c2)cc1]

Another example of a COMT inhibitor is entacapone

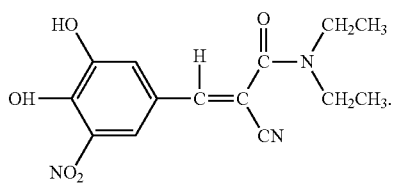 [SMILES: CCN(CC)C(=O)/C(C#N)=C/c1cc(O)c(O)c([N+](=O)[O-])c1]

Pharmaceutically acceptable salts of compounds that are COMT inhibitors can be obtained using standard procedures well known in the art.

The compounds can be formulated as pharmaceutical compositions and administered to a mammalian host, such as a human patient, in a variety of forms adapted to the chosen route of administration, e.g., orally or parenterally, by intravenous, intramuscular, topical or subcutaneous routes.

Thus, the compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2-60% of the weight of a given unit dosage form. The amount of active compound in such therapeutically useful compositions is such that an effective dosage level will be obtained when administered, e.g., either in a single dose or in multiple doses.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the compounds can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, useful for use in treatment will vary not only with the particular compound selected but also with the route of administration, the nature of the condition being treated and the age and condition of the patient and will be ultimately at the discretion of the attendant physician or clinician.

In general, however, a suitable dose will be in the range of from about 50 to about 2,000 mg per day, e.g., from about 50 to about 1,600 mg per day, e.g., from about 50 to about 600 mg per day, e.g., from about 100 to about 300 mg per day, e.g., about 100 or 200 mg per day, e.g., about 140 mg per day. In certain embodiments, tolcapone is administered at a dosage of up to about 600 mg per day. In certain embodiments, entacapone is administered at a dosage of up to about 1,600 mg per day. In certain embodiments, tolcapone is administered from about 100-300 mg/day. In certain embodiments, entacapone is administered from about be 200-1600 mg/day. Such dosages may be administered in a single or in multiple (e.g., 2, 3, 4, 5, 6, 7, or 8) daily administrations.

The compound can be conveniently formulated in unit dosage form; for example, containing 5 to 1000 mg, conveniently 10 to 750 mg, most conveniently, 50 to 500 mg (e.g., 100 or 200 mg) of active ingredient per unit dosage form. In one embodiment, the invention provides the use of a composition comprising a compound of the formulated in such a unit dosage form.

The desired dose may conveniently be presented in a single dose or as divided doses administered at appropriate intervals, for example, as 2, 3, 4, 5, 6, 7, 8 or more sub-doses per day. The sub-dose itself may be further divided, e.g., into a number of discrete loosely spaced administrations; such as multiple tablets.

COMT inhibitors can also be administered in combination with other therapeutic agents.

The invention will now be illustrated by the following non-limiting Example.

EXAMPLES 1 and 2

Tolcapone in the Treatment of Pathological Gambling

In example 1, six subjects have been enrolled in a study to determine the effects of administration of the COMT inhibitor tolcapone on gambling. Subjects receive 100 mg-300 mg of tolcapone by mouth per day for 8 weeks, which can be administered either once per day for the 100 mg dose, or multiple (e.g., 3) times per day for higher doses (e.g., 300 mg dose). Five of the 6 (83%) subjects have "responded" (i.e., greater than 35% on the primary outcome measure, the PG-YBOCS) to tolcapone. In most open-label studies of pathological gambling, response rates are approximately 65%.

Decrease in gambling symptoms was from a mean of 20.4 to 8.0 at endpoint using the PG-YBOCS. This compares to a mean decrease of 6 points on this same scale when used in treatment studies involving other medications.

The mean effective dose was 140 mg/day.

Cognitive measures demonstrate significant improvement on the extradimensional set shift task, which is dependent on the medial prefrontal cortex (in rats) and the dorsal lateral prefrontal cortex (in primates). The cognitive tasks require subjects to disengage responding from the previously correct dimension in favor of responding to a novel dimension. Failure on the task may be due to the inability of the individual to disengage from a previously rewarding process thus perseverating on the incorrect response pattern.

Tolcapone Study (A) Whole Group Analysis, Before and after (EOS) Treatment

|  | Mean ± Standard Deviation (SD) | |
| --- | --- | --- |
|  | Baseline | EOS |
| PG-YBOCS | 21.5 ± 3.11 | 10.25 ± 6.18 |
| IED Stages completed | 9 ± 0 | 9 ± 0 |
| IED Total errors | 12.75 ± 6.5 | 17 ± 7.16 |
| IED Total errors (adjusted) | 12.75 ± 6.5 | 17 ± 7.16 |
| SST Direction errors on stop and go trials | 2.75 ± 4.27 | 6.5 ± 11.03 |
| SST Median correct RT on GO trials | 530.5 ± 132.91 | 529 ± 155.66 |
| SST SSRT (last half) | 166.23 ± 41.87 | 16726 ± 35.33 |
| IED Total errors (stage 6), ID shift | 0.5 ± 1 | 0 ± 0 |
| IED Total errors (stage 8), ED shift | 6.75 ± 5.91 | 3.5 ± 4.51 |

In Example 2, twelve subjects have been enrolled with four of these individuals currently receiving tolcapone and yet to complete the study. Seven of 8 (87.5%) of subjects who have completed the study have "responded" (i.e., greater than 35% on the primary outcome measure, the PG-YBOCS) to tolcapone. In most open-label studies of pathological gambling, response rates are approximately 60-65%.

Decrease in gambling symptoms was from a mean of 20.4 to 9.25 at endpoint using the PG-YBOCS. This compares to a mean decrease of 6 points on this same scale when used in treatment studies involving other medications.

Clinical trial data are listed in Tables 1-4.

TABLE 1

Demographic and Clinical Characteristics of Individuals with Pathological Gambling

|  | Subjects (n = 12) |
| --- | --- |
| Age | |
| Mean (±SD) [range], years | 49.3 (13.2) [27-64] |
| Female, n (%) | 8 (66.7) |

TABLE 1-continued

Demographic and Clinical Characteristics of Individuals with Pathological Gambling

| | Subjects (n = 12) |
|---|---|
| Race/Ethnicity, n (%). | |
| Caucasian | 10 (83.3) |
| Other | 2 (16.7) |
| Marital Status, n (%) | |
| Single | 5 (41.7) |
| Widowed/Separated/Divorced | 7 (58.3) |
| Education, n (%) | |
| High school grad or less | 4 (33.3) |
| Some college | 6 (50) |
| College grad or post-college | 2 (16.7) |
| Age at PG onset | |
| Mean (±SD), [range], years | 36.8 (11.8) [22-55] |
| Primarily strategic gamblers, n (%)[1] | 1 (8.3) |
| Previous treatment for gambling, n (%) | |
| Gamblers Anonymous | 9 (75) |
| Individual Outpatient Therapy | 3 (25) |
| Inpatient/Residential | 1 (8.3) |
| Group Therapy | 2 (16.7) |
| Percentage of gross income lost to gambling in the previous 12 months | |
| Mean % (±SD) | 67.5 (62.1) |
| Time spent gambling each week | |
| Mean (±SD) [range], hours | 12.8 (10.8) [7-38.5] |
| Legal Consequences due to gambling, n (%) | |
| Bankruptcy | 5 (41.7) |
| Writing bad checks | 8 (66.7) |
| Theft | 3 (25) |

[1]Strategic gambling = for example, cards, dice, sports (compared to non-strategic which includes slots, pull tabs).

TABLE 2

Changes on Primary and Secondary Measures

| | Baseline | Endpoint | p-value |
|---|---|---|---|
| Dose of Tolcapone (mg), Mean (±SD) | 100 (0) | 262.5 (74.4) | x |
| PG-YBOCS total score | 20.5 (3.38) | 9.25 (5.3) | 0.0002 |
| PG-YBOCS urges/thought subscale score | 10.88 (2.23) | 5.38 (2.33) | 0.0003 |
| PG-YBOCS behavior Subscale score | 9.63 (3.2) | 3.63 (3.96) | 0.0003 |
| G-SAS total score | 27.13 (7.54) | 18.63 (7.91) | 0.045 |
| HAM-A | 8.88 (3.14) | 5.63 (2.97) | 0.052 |
| HAM-D | 9 (2.67) | 5.63 (3.02) | 0.033 |
| Sheehan Disability Scale total score | 16.75 (6.84) | 5.38 (5.90) | 0.003 |
| Clinical Global Impression Severity | 4.38 (0.74) | 3 (1.07) | 0.0098 |
| CGI-Improvement (Investigator) | x | 1.88 (0.83) | x |
| CGI-Improvement (Patient) | x | 2.19 (1.13) | x |

Mean effective dose = 141 mg/day; (compared to 600 mg/day used for Parkinson's)

TABLE 3

Change in Cigarette Smoking in 6 Nicotine Dependent Problem Gambling Subjects Taking Tolcapone

| Variable | Baseline (n = 6) | 10-Week Endpoint (n = 6) |
|---|---|---|
| Cigarettes smoked per day (mean ± SD) | 25.8 ± 11.1 | 3.3 ± 8.2 |

Neurocognitive Results

Cognitive measures demonstrate significant improvement on the extradimensional set shift task which is dependent on the medial prefrontal cortex (in rats) and the dorsal lateral prefrontal cortex (in primates). The cognitive tasks require subjects to disengage responding from the previously correct dimension in favor of responding to a novel dimension. Failure on the ED task may be due to the inability of the individual to disengage from a previously rewarding process thus perseverating on the incorrect response pattern.

TABLE 4

Performance on Cognitive Tasks in Pathological Gambling Treated with Tolcapone Compared to Age/Gender Matched Controls

| | Pathological Gamblers (PG) | |
|---|---|---|
| | Baseline | Endpoint |
| IDED Stages completed | 8.5 ± 0.92 | 8.86 ± 0.38 |
| IDED total errors (adjusted) | 26.38 ± 21.84 | 20.14 ± 11.77 |
| SST directional errors | 2 ± 3.07 | 4.71 ± 8.24 |
| SST median go reaction time | 470.5 ± 111.67 | 476.64 ± 138.11 |
| SST SSRT | 149.8 ± 41.57 | 161.37 ± 29.11 |

IDED = Intradimensional Extradimensional; SST = Stop Signal Task; SSRT—Stop Signal Reaction Time

EXAMPLE 3

Tolcapone in the Treatment of Kleptomania

Patient was a 60-year old, married, college-educated female with no children. She presented for psychiatric evaluation for "out-of-control" shoplifting that had been going on since early adulthood. Although never arrested for her shoplifting, she reported stealing approximately 90% of the times when she went shopping. Patient primarily stole clothing (usually in sizes that did not fit her) and other personal items such as makeup and hair products. She denied wanting or needing the items and in fact usually discarded them in the trash when she returned home. She reported that when she initially stole items in early adulthood the act gave her a "rush" or a thrill. Over the years, she described the behavior as "automatic" and without awareness for the consequences.

The diagnosis of kleptomania was confirmed using the Structured Clinical Interview for Kleptomania. Patient also underwent a comprehensive psychiatric evaluation using the Structured Clinical Interview for DSM-IV (SCID-I and SCID-II). Patient had a history of major depressive disorder (although she did not meet current criteria) and an avoidant personality disorder. Severity of kleptomania was assessed using the Kleptomania Symptom Assessment Scale (K-SAS) at baseline and periodically through her follow-up. The K-SAS score at baseline was 28 (moderate severity).

Over a period of two years, patient underwent serial trials of several medications. She had a trial of citalopram monotherapy (12 weeks at 60 mg/day), naltrexone (17 weeks total with 6 weeks at peak dose of 150 mg/day monotherapy), naltrexone plus N-acetyl cysteine (100 mg of naltrexone plus 2400 mg of N-acetyl cysteine for 8 weeks), (topiramate monotherapy (12 weeks at 150 mg/day), and topiramate plus risperidone (topiramate 150 mg/day plus resperidone 2 mg/day for 14 weeks). Topiramate monotherapy resulted in some decrease in urges to steal (K-SAS score of 21), but no medication produced any benefit for her behavior and the frequency of her stealing remained unchanged. Patient was started on tolcapone (100 mg/day), a catechol-O-methyl-transferase (COMT) inhibitor as monotherapy. After 3 weeks, patient reported significant reductions in stealing behavior. "I have gone to stores several times without stealing anything." After 6 weeks, the benefit seemed to wane and her dose was increased to 100 mg po bid. After 3 weeks on the higher dose, patient again reported no stealing behavior. She has been maintained on that dose for 5 months without stealing. She reports mild urges to steal when in a store but feels able to control her behavior. Patient's K-SAS score has consistently been 6-8 over the last few months. Laboratory testing every two weeks has demonstrated no changes in alanine aminotransferase or aspartate aminotransferase.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for treating or ameliorating pathological gambling in a human patient, the method comprising: administering to the patient a composition consisting of a therapeutically effective amount of a catechol-O-methyl-transferase inhibitor selected from the group consisting of tolcapone or entacapone to treat or ameliorate the pathological gambling.

2. The method of claim 1, wherein the catechol-O-methyl-transferase inhibitor is administered orally.

3. The method of claim 1, wherein the catechol-O-methyl-transferase inhibitor is administered at a dose of about 100 mg-300 mg per day.

4. The method of claim 1, wherein the catechol-O-methyl-transferase COMT inhibitor is administered at a dose of about 140 mg per day.

* * * * *